US006234023B1

(12) United States Patent
Collins et al.

(10) Patent No.: US 6,234,023 B1
(45) Date of Patent: May 22, 2001

(54) ULTRASONIC MONITORING TECHNIQUE FOR CONTAINERS AND APPARATUS TO CARRY IT OUT

(75) Inventors: Andrew P. Collins, Worcester; Steven M Dixon, West Midlands; Christopher Edwards, Coventry; Stuart B Palmer, Warwickshire, all of (GB)

(73) Assignee: M & A Packaging Services Limited, Worcestershire (GB)

( * ) Notice: Subject to any disclaimer, the term of this patent is extended or adjusted under 35 U.S.C. 154(b) by 0 days.

(21) Appl. No.: 09/068,244

(22) PCT Filed: Nov. 11, 1996

(86) PCT No.: PCT/GB96/02781

§ 371 Date: Oct. 19, 1998

§ 102(e) Date: Oct. 19, 1998

(87) PCT Pub. No.: WO97/17591

PCT Pub. Date: May 15, 1997

(30) Foreign Application Priority Data

Nov. 9, 1995 (GB) .................................................. 9522949

(51) Int. Cl.[7] .................................................. G01N 29/18
(52) U.S. Cl. ........................... 73/597; 73/643; 73/290 V; 209/524; 209/590
(58) Field of Search ................................. 73/290 V, 643, 73/598, 597; 209/590, 524, 529

(56) References Cited

U.S. PATENT DOCUMENTS

| | | | |
|---|---|---|---|
| 2,960,678 | | 11/1960 | Beard et al. ........................ 73/290 V |
| 4,223,790 | * | 9/1980 | Yoshida ................................ 209/590 |
| 4,821,573 | * | 4/1989 | Nagata et al. ........................... 73/597 |
| 4,864,848 | * | 9/1989 | Irvine .................................... 73/45.4 |
| 4,901,245 | * | 2/1990 | Olson et al. .......................... 364/509 |
| 5,000,046 | | 3/1991 | Garcia et al. ........................... 73/597 |
| 5,602,890 | * | 2/1997 | Gray et al. ............................... 378/57 |
| 5,608,164 | * | 3/1997 | MacLauchlan ......................... 73/599 |
| 5,836,192 | * | 11/1998 | Getman et al. ..................... 73/290 V |
| 5,929,337 | * | 7/1999 | Collins et al. .......................... 73/597 |

FOREIGN PATENT DOCUMENTS

| | | |
|---|---|---|
| 0 075 492 A1 | 3/1983 | (EP) . |
| 0 360 449 | 3/1990 | (EP) . |
| 0 436 207 A1 | 7/1991 | (EP) . |
| 0614 084 A1 | 9/1994 | (EP) . |

OTHER PUBLICATIONS

D.A. Hutchins, M.D.C. Moles, G.S. Taylor and S.B. Palmer; "Non–Contact Ultrasonic inspection of diffusion bonds in titanium"; Ultrasonics vol. 29, Jul. 1991, pp. 294–301.

* cited by examiner

Primary Examiner—Hezron Williams
Assistant Examiner—Rose M. Miller
(74) Attorney, Agent, or Firm—Woodard, Emhardt, Naughton, Moriarty & McNett (57) ABSTRACT

The invention provides an apparatus and method for fill level monitoring in which the height of contents in a container (10) is monitored. The apparatus comprises an ultrasound reciever (30) and signal processing means (50–56) adapted to receive signals from the receiver, the arrangement being such that the signal processing means (50–56) identifies a first signal (32), in use, which is representative of a wavefront (26) transmitted through the contents of the container (10) independently of the height of the contents in the container (10), and a second signal (34) that is representative of a wavefront (24) that is reflected from the interface (22) between the surface of the contents in the container (10) and the environment above the contents, and in which the signal processing means (50–56) uses the difference in travel time for the two wavefronts (24, 26) to provide a measurement of the level of the contents in the container (10). A plasma generation system comprising a pulsed laser (99) and a target (101) in front of the container (102) is also disclosed, the plasma (103) creating ultrasound in the container (102).

35 Claims, 10 Drawing Sheets

ULTRASONIC MONITORING TECHNIQUE FOR CONTAINERS AND APPARATUS TO CARRY IT OUT

This invention relates to an ultrasonic monitoring technique for containers, and to apparatus to carry it out. It especially (but not exclusively) relates to apparatus for, and a method of, measuring the fill level of a substance in a container, preferably of a liquid in a container that is moving on a production line.

The invention arose out of a consideration of the process of filling beverage cans with beverage and will be discussed in that context, but it will be apparent that it is applicable more widely than that.

In conventional beverage can filling lines the amount of beverage that is put in the can before it is sealed is determined by a number of variables. These include (but are not restricted to) a) container variables (line speed/can size etc.) b) filler variables (including filler valve physical characteristics and control techniques) and c) product variables. Any changes in these variables may affect the fill level within the container and so the amount of beverage in a container can vary. Fill level detectors are used to measure the level of beverage in a can, usually a sealed can. At present suitable fill level detectors use X-rays, or gamma rays. Both of these are health hazards and their use is carefully controlled.

According to a first aspect of the invention we provide fill level monitoring apparatus adapted to monitor the height of contents in a container, the apparatus comprising an ultrasound receiver, and signal processing means adapted to receive signals from the receiver; the arrangement being such that the signal processing means identifies a first signal, in use, which is representative of a first ultrasonic wave which has been transmitted through the contents of the container independently of the height of the contents in the container, and a second signal that is representative of a second ultrasonic wave that has been reflected from the interface between the surface of the contents in the container and the environment above the contents, and in which the signal processing means uses the difference in transit times for the two waves to provide an indication of the level of the contents in the container.

Preferably the dimensions of the container are known and these are used in conjunction with the transit times for the two waves to provide an indication of the level of the contents in the container. Preferably an indication of the level of the contents is provided which is independent of the temperature or composition of the contents.

Preferably the apparatus includes ultrasound generation means, but in some cases that may be additional to the detection part of the apparatus.

The container may be moving during the transmission of the first and/or second ultrasonic waves.

Preferably the ultrasonic waves which are detected as the first and second signals are generated simultaneously by the ultrasound generation means. The ultrasonic waves that are detected as the first and second signals may be different parts of the same wavefront.

The apparatus is preferably capable of generating and/or detecting a second set of first and second waves shortly after the first set (e.g. 5 ms after). The apparatus is preferably capable of performing a second measurement on the same container shortly after the first measurement (e.g. 5 ms after).

The ultrasound generation means preferably is a laser, or includes a laser, especially, but not exclusively a $CO_2$ laser. TEA $CO_2$ lasers have the output characteristics and repetition rate that we desire for an embodiment of the invention (about 40 or 50 cycles per second).

The ultrasound receiver and/or ultrasound generation means is preferably couplant free, (by couplant free we mean no solid or liquid couplant exists between the ultrasound receiver and the container, and/or between the ultrasound generation means and the container). However, in principle liquid coupled, and even mechanical contact detectors/ultrasound producers are envisaged, but they cannot work in fast running canning lines as well as do couplant free detectors/emitters.

The apparatus is preferably arranged such that the ultrasound receiver is disposed to the side of a container. Preferably the ultrasound generation means is, in use, to the side of the container, most preferably "radial" to the container. The receiver and generation means may be on opposite sides of the container, or when viewed from above the container they may be at an angle away from the 180° straight-through configuration.

The receiver and the generation means may be at substantially the same height relative to the container. Alternatively, we may prefer to have the receiver at a different height to that of the generation means. This may be used to improve the resolution of the first and second signals.

Preferably the receiver is not more than about 10 mm from the container when the ultrasound waves that generate the first and second signals are detected, most preferably not more than 5 mm, 2 mm or 1 mm away.

Preferably the generation means produces a divergent ultrasound wavefront.

The first and second signals may be derived from one or more ultrasonic wavefronts, preferably a single wavefront, generated at the same location on the container or at a geometrically small area of the container (e.g. about 4 mm$^2$). Preferably the receiver detects ultrasound from only a localised height of the container, most preferably over a height of 4 mm or less, or 3 mm or less, or 2 mm or less.

The apparatus preferably includes a broadband ultrasound receiver. Most preferably the receiver can detect from low frequency to at least 1 MHz, and preferably above 1 MHz. The receiver may be able to receive from DC to above 1 MHz.

The ultrasound generation means preferably is capable of producing a broadband signal, in the same range of frequencies as mentioned above for the receiver.

The apparatus preferably has an electronic signal filter, such as a band pass filter. It preferably has a signal amplifier, which may be tuned to the same band of frequencies as the receiver.

The receiver may be an EMAT (electromagnetic acoustic transducer). An EMAT may be the receiver of choice if the container is to be a metal can. The EMAT may be polarised preferably to give maximum sensitivity to top surface reflections of ultrasound from the upper surface of the contents of the container.

Preferably the container is a metal can.

There is preferably a feedback mechanism whereby the apparatus can feed back signals, derived from the first and second signals, to control apparatus for subsequent use in controlling the filling operation or filling apparatus.

According to a second aspect of the invention we provide a fill level monitoring apparatus adapted to monitor the height of contents in a container, comprising an ultrasound receiver and signal processing means adapted to receive signals from the receiver, the arrangement being such that the signal processing means identifies a signal which is representative of an ultrasonic wave which has been reflected from the interface between the surface of the contents of the container and the environment above the contents, and in which the signal processing means uses the transit time of the ultrasound wave to provide an indication of the level of the contents in the container.

We can get an indication of the fill level of the contents in the container from just the "top surface" reflection. If we know the diameter of the container and the velocity of sound in the contents of the container we can calculate the height of the surface above the datum point. The container diameter and the velocity of sound for a medium can be, in some embodiments, pre-programmed into the signal processing means.

The velocity of sound in a medium varies as a function of the temperature of that medium. The temperature of the contents of a container on a production line as it passes a point on the line may vary from one container to another.

We could measure the temperature of the contents of the container and use that in an algorithm or in an appropriate look up table. We prefer, however, to measure the arrival times of the two detection signals indicative of two different waves that have travelled different paths, using that (together with a knowledge of the dimensions of the container and geometry of the paths taken by the waves that generated the signals) to eliminate the need to know the temperature of the contents of the container.

In one preferred embodiment the path geometry for two different paths is known, and the time difference between arrival of the two signals at the detector is known, and hence the height of the surface of the contents above a datum point can be evaluated by taking the time difference and applying an appropriate algorithm, or inspecting an appropriate look up table.

According to another aspect of the invention we provide a container filling line comprising container filling means adapted to deliver contents to a container, control means controlling the operation of the container filling means, and fill-level monitoring apparatus in accordance with the first or second aspect of the invention.

The filling line preferably includes container rejection means adapted to remove a container from the line. Tracking means may be provided to track a container from the point where it is identified as being a reject to the point at which it is actually rejected.

According to another aspect of the invention we provide a method of monitoring the fill level of contents in a container comprising generating ultrasound waves in the container, detecting a straight through ultrasound wave, detecting a top surface reflected wave from the top surface of the contents of the container, and determining the time difference between the two waves in order to obtain an indication of the level of the contents in the container.

According to another aspect of the invention we provide a method of monitoring the height of contents in a container comprising generating an ultrasonic wave; reflecting it from the interface between the contents of the container and the environmnent above the contents; determining the transit time of the reflected wave; and using a knowledge of the geometry of the container and of the transit time to determine the height of the contents.

Preferably the dimensions of the container are known and are used in conjunction with the arrival times of the two waves to obtain an indication of the level of the contents in the container. The method then compensates for variations in the temperature or composition of the contents.

According to a further aspect of the present invention, a non-contact apparatus for monitoring contents of a container is provided comprising non-contact ultrasonic wave generation means adapted to produce in use an ultrasonic wave in a container being monitored, non-contact ultrasonic wave detector means adapted to detect an ultrasonic wave and to generate a detection signal dependent upon the ultrasonic wave which is detected, and signal processing means adapted to process the detection signal generated by the ultrasonic wave detector means in order to detect a particular characteristic of the contents of the container, and in which the wave generation means comprises plasma producing means adapted to produce a plasma at or near the surface of the container.

Having detector means and processing means may be optional. We may provide just the ultrasound producing system.

The plasma producing means may comprise a laser. Alternatively it could be an electrical source (e.g. high voltage discharge).

The plasma producing means may produce plasma, e.g. by a high energy strike, at the container surface, for example by having a laser beam or electrical spark hit the container. However, we prefer to have the plasma generated at a region close to the container, but not actually at the wall of the container. Spaced plasma generation means are preferably provided to achieve this. The spaced plasma generation means may comprise a target that is not the container (e.g. a member between the energy source that produces the energy strike and the container). We may simply have a target plate next to the container, the laser beam (or other energy source) striking the target plate instead of the container directly.

One advantage of the plasma target system is that we have found that by using plasma to generate ultrasound no mark, or much less of a mark, can be made on the container (direct impact with a laser beam of sufficient intensity to generate ultrasound can mark the surface of a container).

The laser is preferably adapted to operate in pulsed mode. Pulsed lasers can fire many times per second. This enables us to monitor many containers per second, possibly 30, 40 or 50 per second.

According to a still further aspect, the present invention provides a couplant-free method of monitoring the contents of a container comprising, firstly, generating an ultrasonic wave within the contents of the container, secondly, detecting an ultrasonic wave at a localised region of the container and producing a detection signal dependent upon the detected ultrasonic wave, and thirdly processing the detection signal in order to determine a particular characteristic of the contents of the container, the ultrasonic wave being generated by the impact of a laser beam or by a plasma generating device adapted to generate plasma at or slightly spaced from the container.

Preferably the ultrasonic wave is detected at a localised region at the outer surface of the container.

According to another aspect of the invention we provide an ultrasound source comprising an energy source adapted to produce a pulse of energy and a target at which plasma is generated, the arrangement being such that in use the target is interposed between the energy source and an article that is to have ultrasound generated in it, and the energy source produces in use an energy strike that impinges on the target, as opposed to impinging directly on the article, generating a plasma at the target, which plasma generates ultrasound in the article.

The target is preferably spaced from the article. The spacing may be of the order of 1 mm, 2 mm, 3 mm, 4 mm, 5 mm, or above.

The target may be moveable. It may be replaceable.

Focusing means may be provided to focus the energy strike onto the target. The energy source may be a laser.

According to another aspect of the invention we provide a non-contact method of inspecting an article Comprising, firstly, generating an ultrasonic wave within a portion of the article, secondly, detecting an ultrasonic wave in a portion of the article and producing a detection signal dependent upon the detected ultrasonic signal, and thirdly processing the detection signal in order to detect a particular characteristic of the article, the ultrasonic wave being generated by the impact of a laser beam, or electric discharge, or by a plasma generating means adapted to generate plasm a spaced from the article.

Thus we may inspect things that are not containers, for example castings. Using plasma-generated ultrasound helps to avoid marking the article during ultrasound inspection.

The title of this patent application is not to be taken as restricting this last aspect of the invention just to inspecting containers.

The invention will now be illustrated by way of example only with reference to the accompanying drawings of which.

The invention can be thought of as using a couplant free ultrasonic technique for measuring the fill-level in containers on a moving production line.

The system, according to one embodiment consists of a couplant free means of generating an ultrasonic wave in a moving container and a couplant free means of detecting the ultrasonic waves propagating via a plurality of ultrasonic paths through the contents of the container. The general technique is to measure the time difference between two ultrasonic arrivals, one travelling to the detector directly, the other having been reflected from the gas-liquid interface at the liquid level (Top Surface Reflection, TSR). As the liquid level changes, the temporal separation of the two ultrasonic pulses will change correspondingly. The displacement components normal to the container surface for the direct ultrasonic wave and TSR ultrasonic wave are preferentially measured.

It will be appreciated that although primarily used for liquids the technique can be used for any medium that permits the propagation of longitudinal ultrasonic waves through the bulk of that medium. "Liquid" should be interpreted with that in mind. The liquid need not (indeed usually will not) completely fill the container: there may be a gas in a space above the liquid surface in a sealed container.

Figure 1:
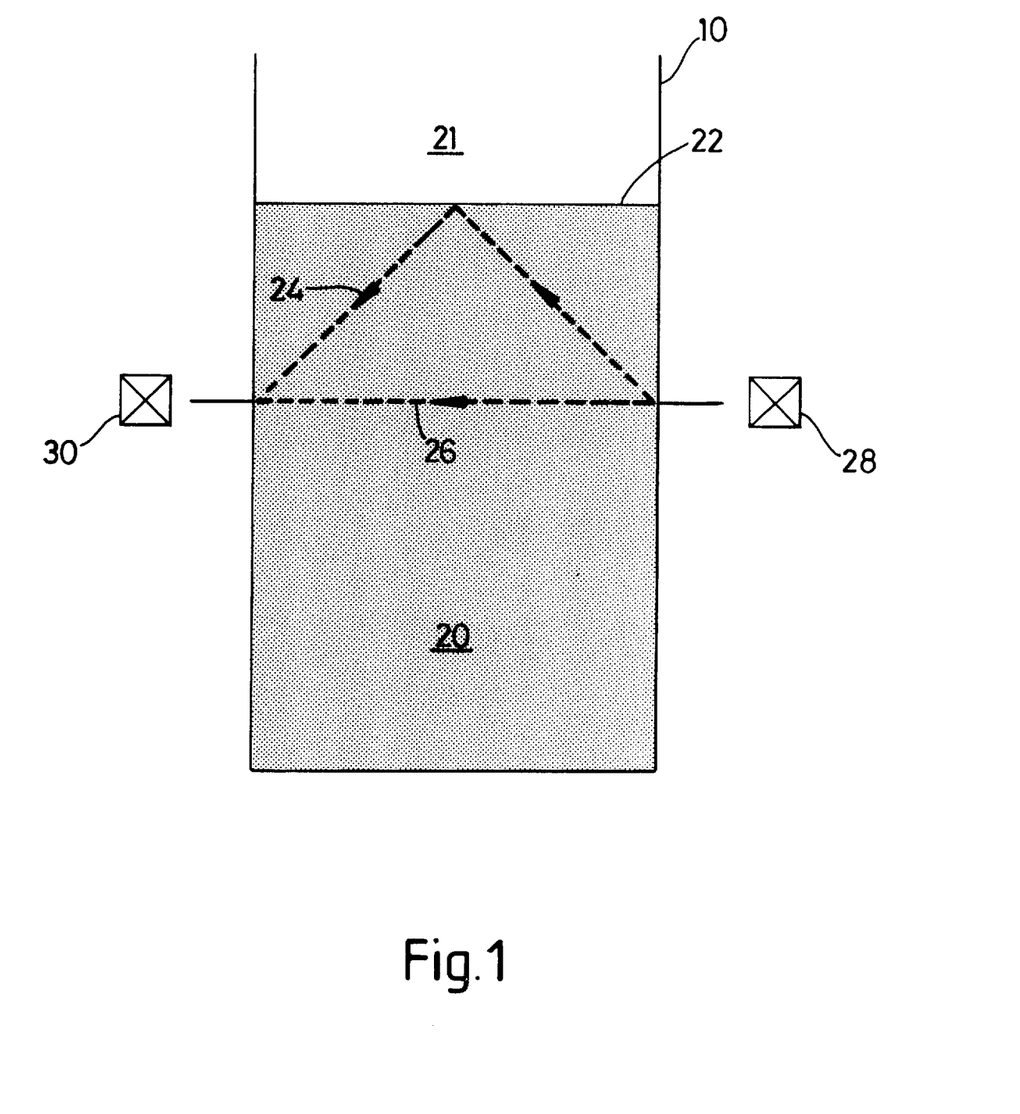
FIG. 1 shows schematically the principle of using ultrasound wave transit time differences to determine fill height in a moving can.

One particular geometry that is suitable for such a liquid level measurement is shown in FIG. 1. An open can body 10, having liquid 20 e.g. beer and gas 21 therein, is shown. The can end has not yet been fixed to the can (of course it will be appreciated that the technique will work whether or not the can is sealed). An ultrasonic source 28 provides ultrasonic waves 24, 26 in the liquid 20, and these are received by an ultrasonic detector 30, which in turn generates electrical signals representative of the waves. The "transit time" of the TSR wave 24 reflected from the gas-liquid interface 22 is longer than that of the direct wave 26. This can be used to indicate the level to which the can 10 is filled.

Figure 2:
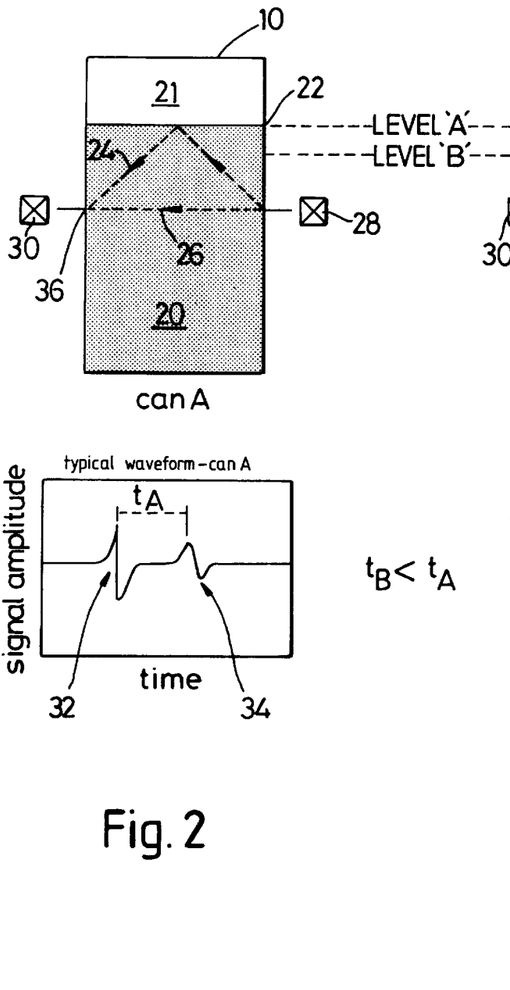
FIGS. 2 and 2' show the difference in time between peaks for signal representative of straight through and Top Surface Reflection (TRS) waves in a can filled to two different levels.

FIGS. 2 and 2' illustrate how the time separation between the TSR 24 and direct 26 ultrasonic waves may change with changes in liquid level. The time difference $t_A$ between the electrical signal 32 representative of the direct wave 26 and the electrical signal 34 representative of the TSR wave 24 is greater than the corresponding time difference $t_B$ which relates to a container with less liquid above the datum point 36 of the detector.

In order to obtain high accuracy in the temporal separation measurement it is desirable to have one ultrasonic source simultaneously generate the two ultrasonic waves from the same localised position on the surface of the container. The ultrasonic field produced by such a source must have some component that travels to the detector via a path independent of liquid level, and some component that has an ultrasonic path dependent upon the liquid level. This could be achieved by using one localised ultrasonic source that generates a divergent ultrasonic wavefront in the container contents (see FIG. 3) from which both detected ultrasonic waves are derived, and detecting the waves at the same localised detection position at the surface of the container. This could also be achieved by an ultrasonic source that has strong guided components off-axis to the container surface normal, and along the direction of the surface normal (see FIG. 4). It is possible to use an array of ultrasonic generators to achieve such a field. An array of detectors may be used, but we prefer to have a single detector with a small active area.

Figure 3:
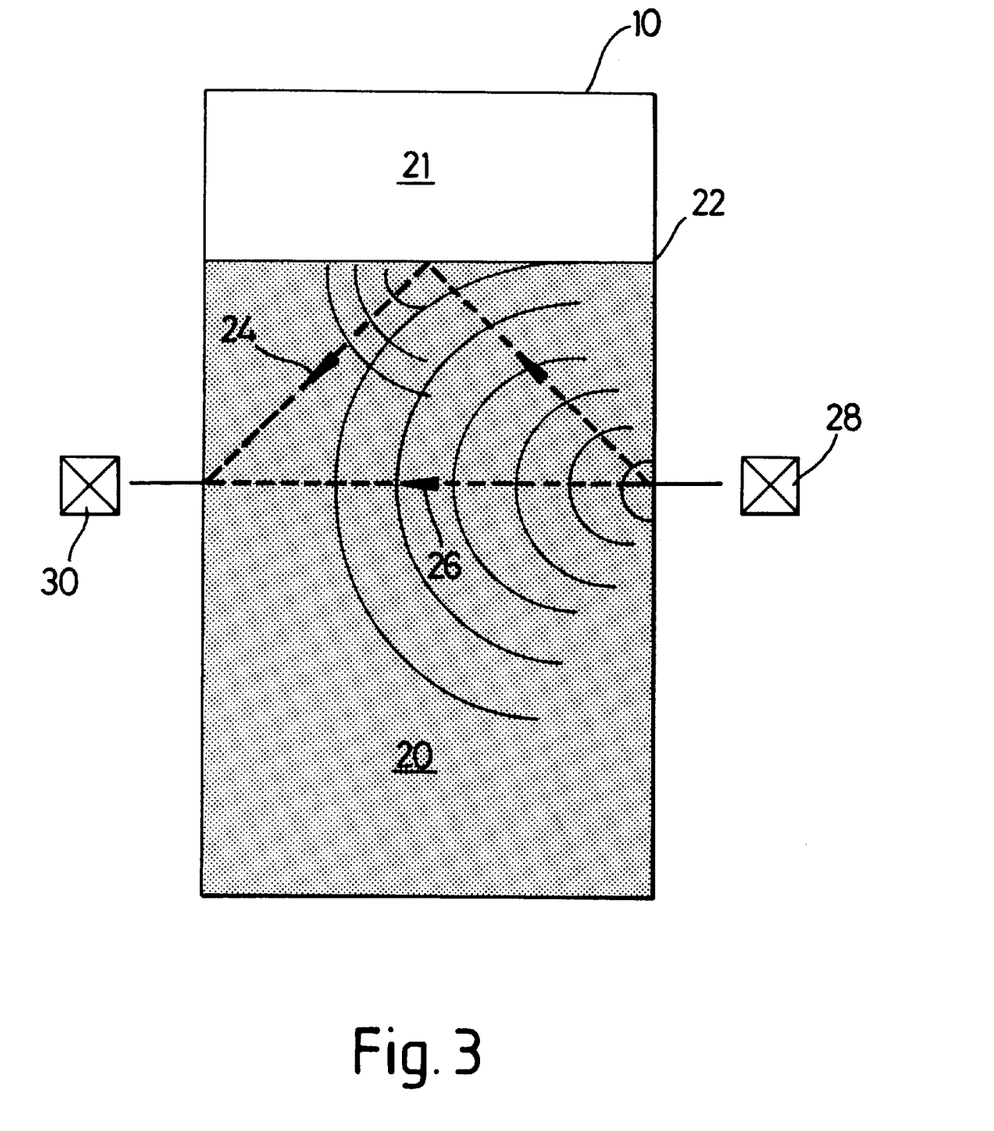
FIG. 3 illustrates a simplified divergent ultrasound wavefront in a can.
Figure 4:
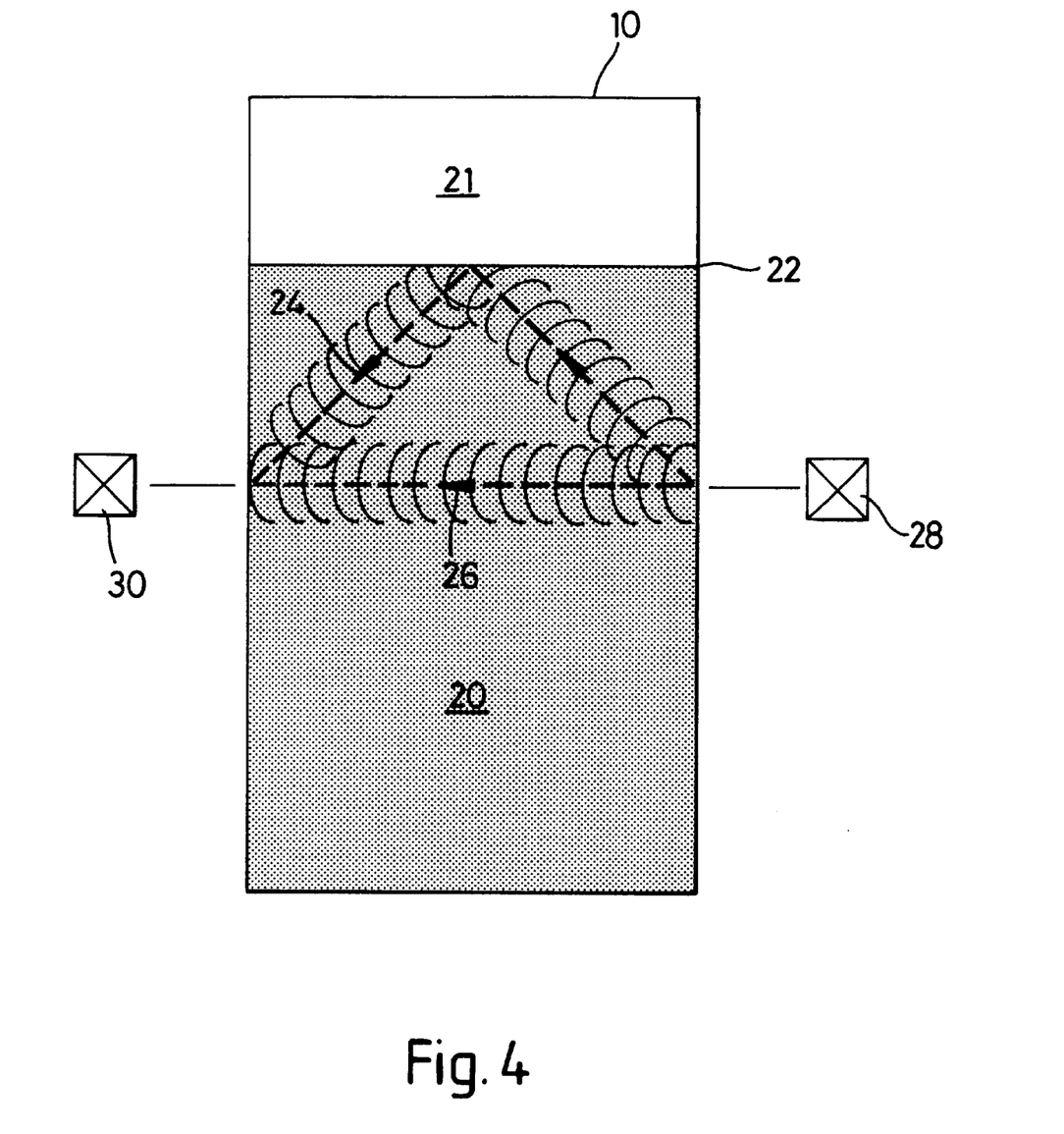
FIG. 4 shows schematically a directional ultrasound fill level system which preferentially emits ultrasound in the straight-through and expected Top Surface Reflection directions.

The divergent field will have a range of TSR path lengths from the gas-liquid interface over the entire range of possible angles. The reason that a distinct signal can be detected when using a divergent ultrasonic field is due to the geometry of the system and the scattering of the ultrasonic wave from the liquid-gas interface. A simplified explanation is that the ultrasonic wave incident on the liquid-gas interface will reflect at an angle to the normal of the interface that is equal to the incident angle of the propagation direction of the wave to the interface normal. As the active ultrasonic detector area is finite, then a finite range of these reflections will be detected. Detecting over a range of incident angles increases the signal amplitude but also leads to signal broadening. We may prefer to detect over only a narrow range of incident angles.

It is preferred to have geometrically small (e.g. about 2–4 mm high and about 10–20 mm wide) active areas at the generation point and detection point of the ultrasonic waves. This reduces broadening of the electrical signals representative of the ultrasonic waves and hence can make the measurement of temporal separation easier and more accurate. It will be appreciated that different detectors may have different optimum sites relative to a container. The size of the generation point and detection point in the direction of the height of the container is more important than their width.

The velocity of ultrasound in liquids is over one thousand times greater than the typical velocity of a container on a high speed production line. This essentially makes the ultrasonic measurement an instantaneous technique compared to the distance that a container will have moved on the production line during the time taken to measure and analyse the ultrasonic waves. The measurement can of course also be performed statically.

It is preferred that the ultrasonic system be broadband, containing significant frequency content from DC to above 1 MHz. The frequency content of the broadband ultrasonic source varies from DC to over 1 MHz. The broadband ultrasonic receiver has a frequency response from DC to above 1 MHz but may be limited by a band pass filter to remove signals from unwanted mechanical vibrations and electrical noise. The definition of broadband in this patent is that the frequency content has measurable and significant frequency components from DC to above 1 MHz. This improves the accuracy of the temporal separation measurement between the two different ultrasonic path lengths of the direct path and TSR path.

Figure 5:
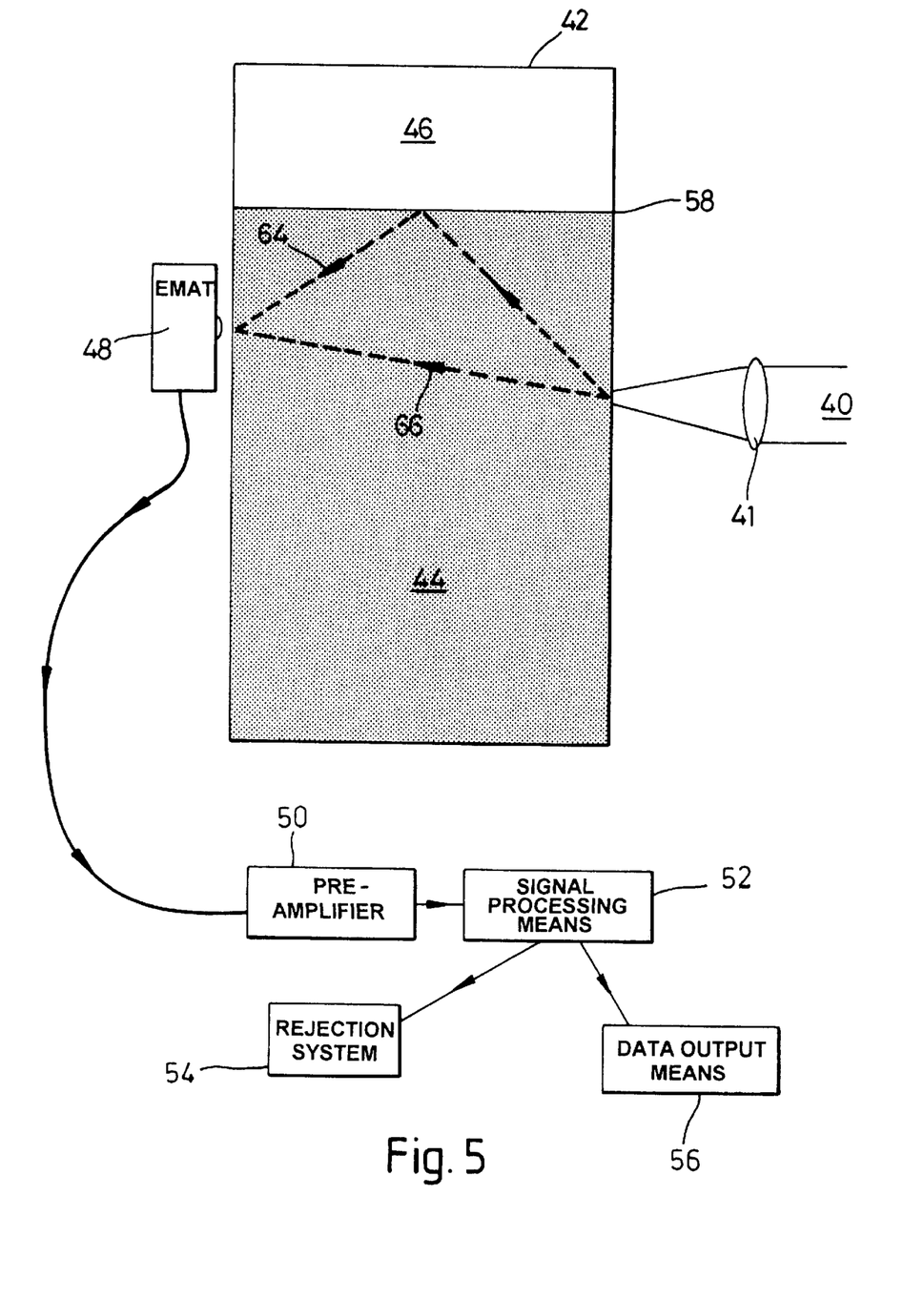
FIG. 5 schematically illustrates one embodiment of the invention.

FIG. 5 illustrates one embodiment of the invention in which the ultrasonic source is a TEA $CO_2$ laser beam 40 focused by a lens 41 to form a localised broadband longitudinal ultrasonic source on a beverage can 42 moving on a canning line and containing liquid 44 and gas 46. The couplant free detector in this embodiment is a broadband electromagnetic acoustic transducer (EMAT) 48 at the opposite side of the can 42, which is designed to detect longitudinal waves in this particular geometry. A preamplifier 50 amplifies the signals from the EMAT and is also broadband in frequency response. Digitisation and signal processing means 52, a rejection system 54 and feedback and data output means 56 are also provided. The laser beam impact site is positioned on the opposite side of the can 42 to the EMAT 48 such that both detector and laser beam pulse site are below the gas-liquid interface 58.

Figure 6:
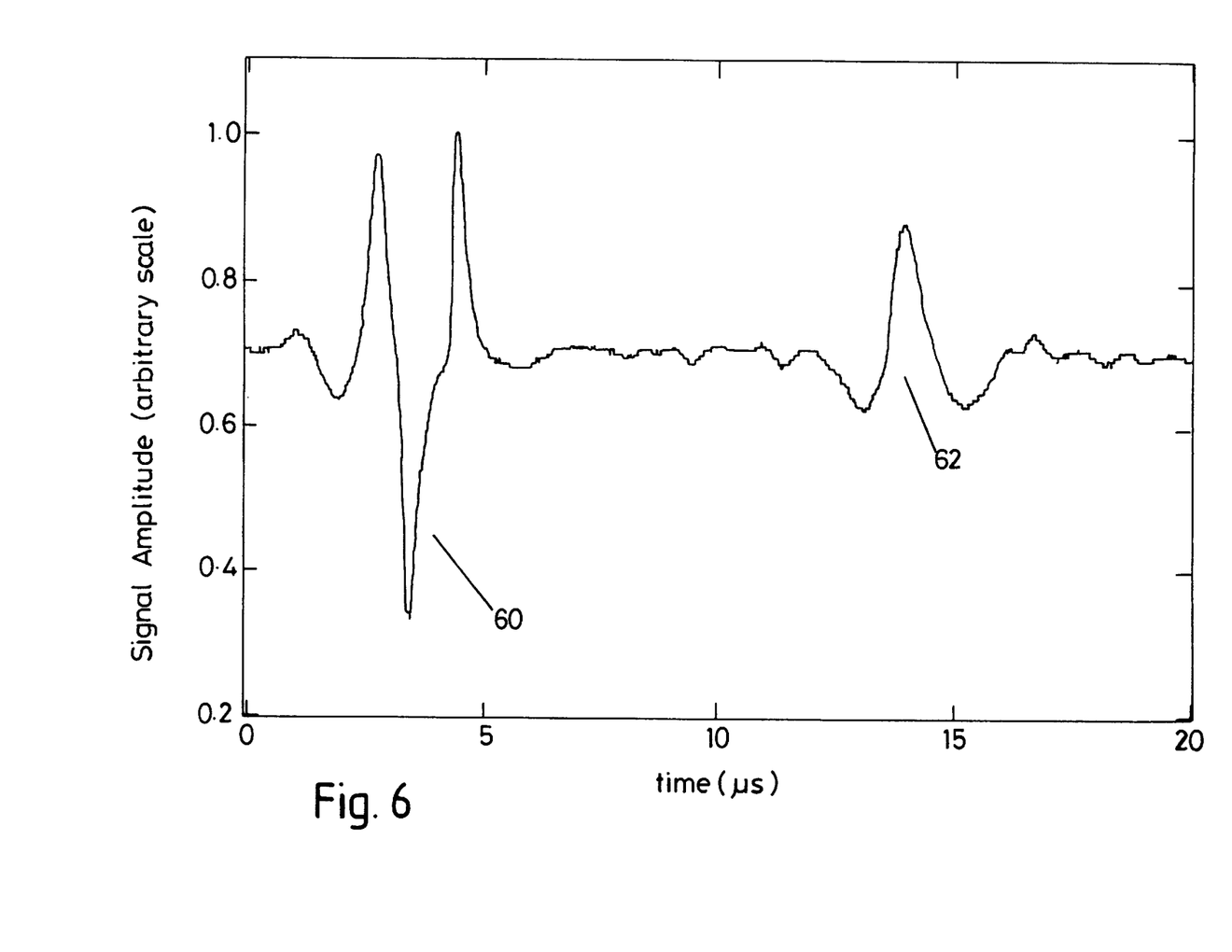
FIG. 6 illustrates the signal detected in trials from the embodiment of FIG. 5.

The ultrasound detector and source need not be at the same level and indeed in this embodiment are not at the same level. Quite often it is advantageous to have the detector and source at different levels to alter the observed relative amplitudes and separations of the signals representative of the direct ultrasonic wave and the TSR wave that arises from the reflection at the gas-liquid interface. The EMAT 48 is polarised to give maximum sensitivity to the signal representative of the TSR wave 64 and minimise signals arising from other ultrasound paths such as guided waves in the can skin itself. A waveform containing an electrical signal 60 representative of the direct ultrasonic wave 66 and an electrical signal 62 representative of the TSR ultrasonic wave 64 is shown in FIG. 6.

Figure 7:
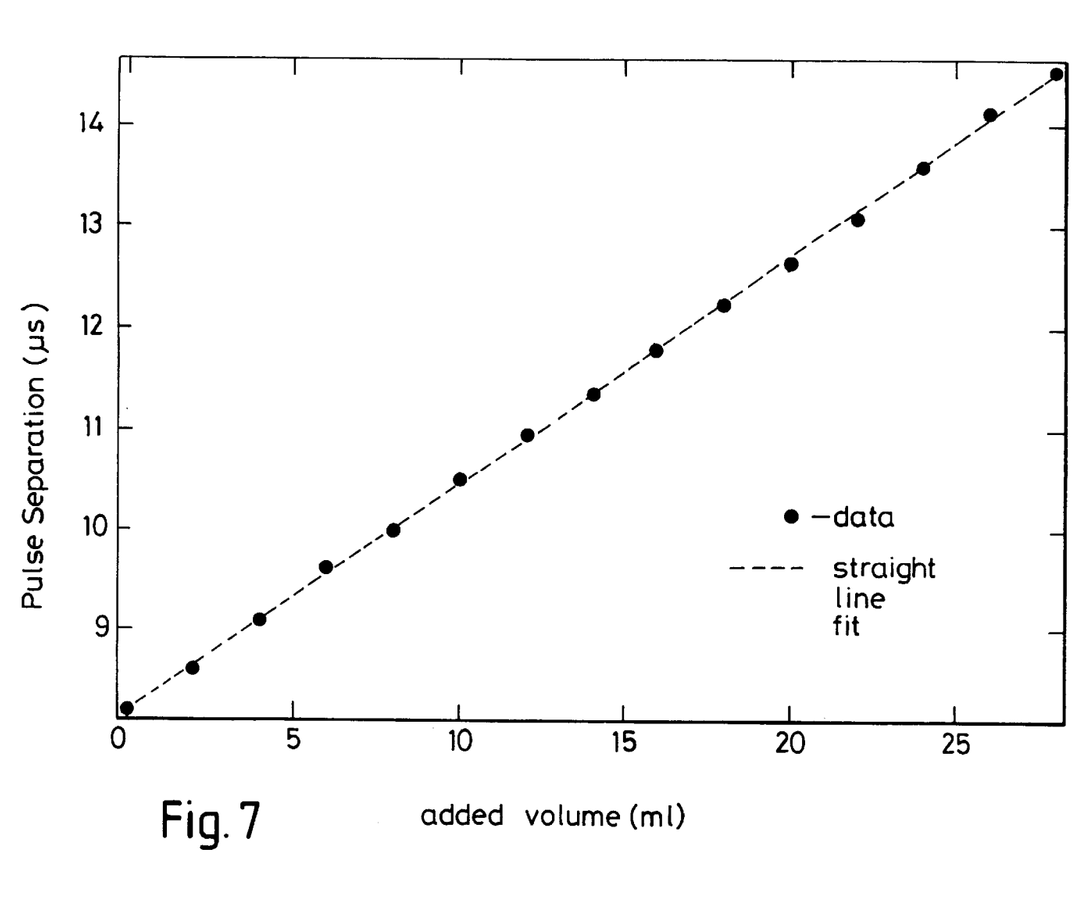
FIG. 7 illustrates test results showing how, for the particular geometry of the embodiment of FIG. 5, the signal separation is a linear function of the additional volume of content in a container.

A plot of measured time separation (between the electrical signals representing the TSR and the direct ultrasonic waves), versus volume of water added to a can of constant cross-sectional area already containing water is shown in FIG. 7. The characteristics of the plot will change as the relative positions of liquid level, EMAT and laser beam impact point are varied, and as the composition of the liquid changes. This type of measurement could be used as a calibration for all successive measurements made on cans containing the same liquid.

While the apparatus described will also generate ultrasonic waves in glass, plastic or paper containers the EMAT transducer can only operate on metal containers. Other types of detectors that could be employed for these cases include a modified wheel probe (used as an ultrasonic generator and/or detector), and an air coupled transducer (ACT). An ACT can today be used only as a detector due to its currently low efficiency.

As ultrasonic generation sources can operate at high repetition rates, the technique described above lends itself to the rapid automated inspection of containers on production lines. The data from the signal processing of the ultrasonic waves can be used in feedback to control other processes on a production line.

Other ultrasound generation sources could be used (e.g. electric spark strike).

Figure 8:
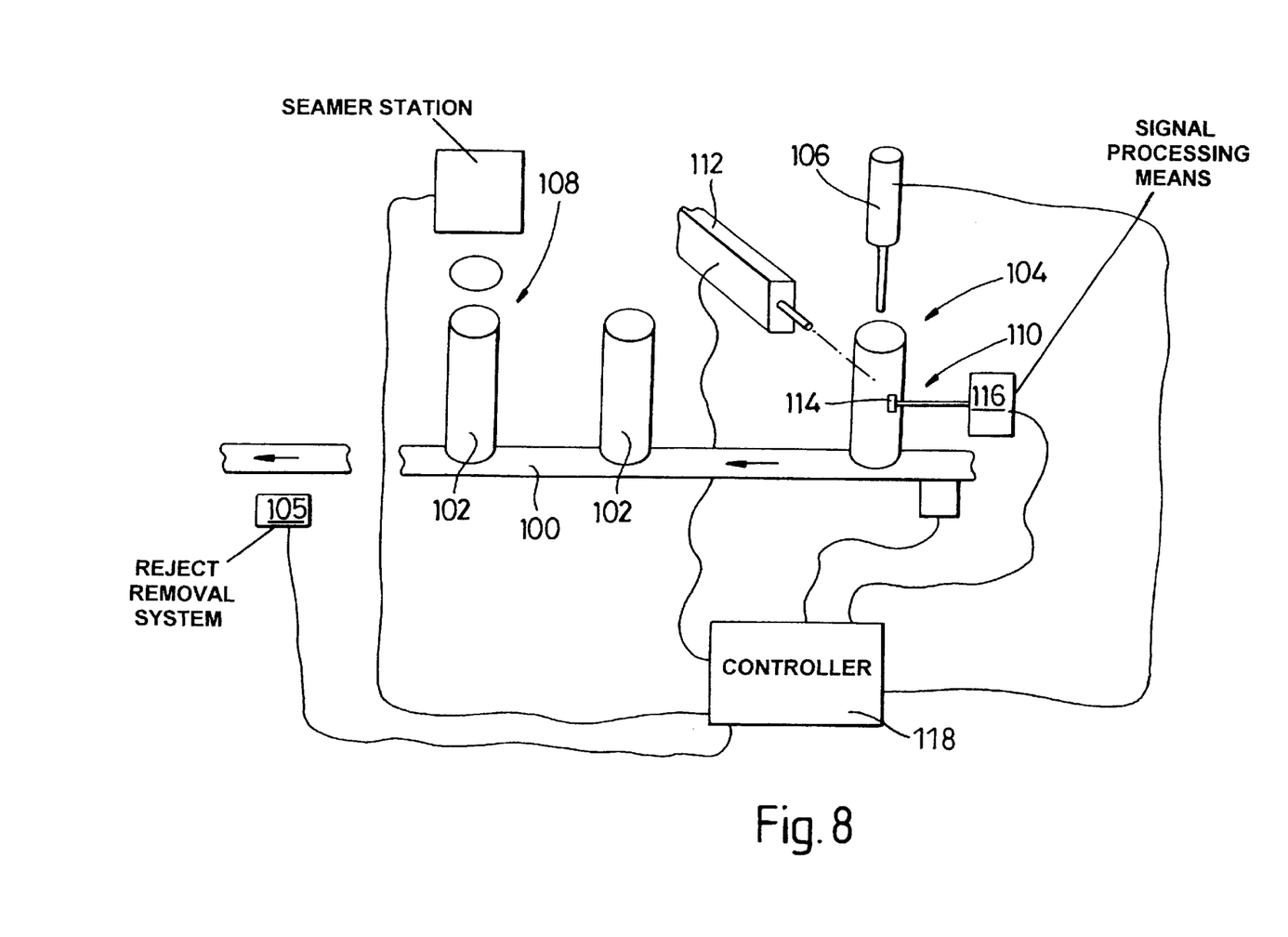
FIG. 8 schematically illustrates a can filling line fitted with the embodiment of FIG. 5.

FIG. 8 shows, schematically, a beer (or other beverage) can filling line. A conveyor 100 moves cans (or other containers) 102 past a filling station 104 (normally a rotary carousel but shown as a single station for clarity) provided with a beer delivery pipe 106. Containers can be presented this way in a continuous process at speeds of up to 3000 per minute. They are then conveyed to a seamer station 108 where a can end is fitted and sealed to the body of the can. A reject removal system 105 is provided downstream for removing cans that do not contain sufficient beer.

The filling station 104 has a fill level detection system 110 which comprises a TEA $CO_2$ laser 112, and EMAT 114, and signal processing means 116. An output signal from the signal processing means is fed to a controller 118 which controls the operation of the beer delivery pipe 106 (and also the conveyor 100, the seamer station 108, and the reject system 105).

The controller 118 operates the beer delivery pipe 106 until the fill-level detection sends a signal to the controller indicating that the beer has reached the desired level, at which point the beer supply is shut off for that can. This enables us to fill each can to a desired level and variations in beer supply pressure/other can-filling factors are automatically compensated since we use feedback from the actual level of beer in the can.

We would envisage supplying the laser, EMAT and signal processing means 116 as a kit for original equipment, and for retro fitting to existing canning/container filling lines.

In order to generate ultrasound in a material, the material must be 'shocked' or stressed. The frequency content of the ultrasound generated will be governed by the rate at which such a stressed state is achieved. For example a periodic mechanical shock of time period one microsecond would generate an ultrasonic wave predominantly of frequency one megahertz. The frequency content of a temporally spike-like ultrasonic generation mechanism contains a range of frequencies and is termed broadband. Making the generating spike sharper in time domain increases the magnitude of the higher frequency ultrasonic components in the resulting ultrasonic wave.

Pulsed lasers can be used to generate ultrasonic waves by rapidly stressing the surface or surface layer of a sample when directed onto that sample. If the laser beam is of sufficient energy density at the sample surface it can generate a plasma, which may comprise particles that have derived from the sample surface and the surrounding atmosphere at that point. This plasma has a net resultant force normal to the surface of the sample and thus predominantly generates a longitudinal wave in the sample. This mode of laser generated ultrasound is said to be in the ablative regime. At low laser energy densities the illuminated area of the sample undergoes a rapid heating, and the ultrasound mode generated is predominantly a shear wave mode in a rigid medium.

The high energy density required to form a plasma on a sample surface usually requires the incident pulsed laser beam to be focused. One problem with this type of ultrasonic generation of longitudinal waves is that the surface of the sample may absorb significant amounts of the incident energy and be in some way damaged. This would be the case for instance when a TEA $CO_2$ laser is focused onto a painted metal surface, where the paint would be damaged or removed from the surface.

A technique of using a plasma to generate ultrasound without damaging the sample surface has been developed. The technique exploits the fact that a plasma is a hot expanding volume of particles, and directs the plasma onto the sample surface without exposing that surface to the laser beam. This is achieved by Generating the plasma on a target in front of or close to the sample in which the ultrasound is to be generated. This can help to avoid marking the sample.

Figure 9:
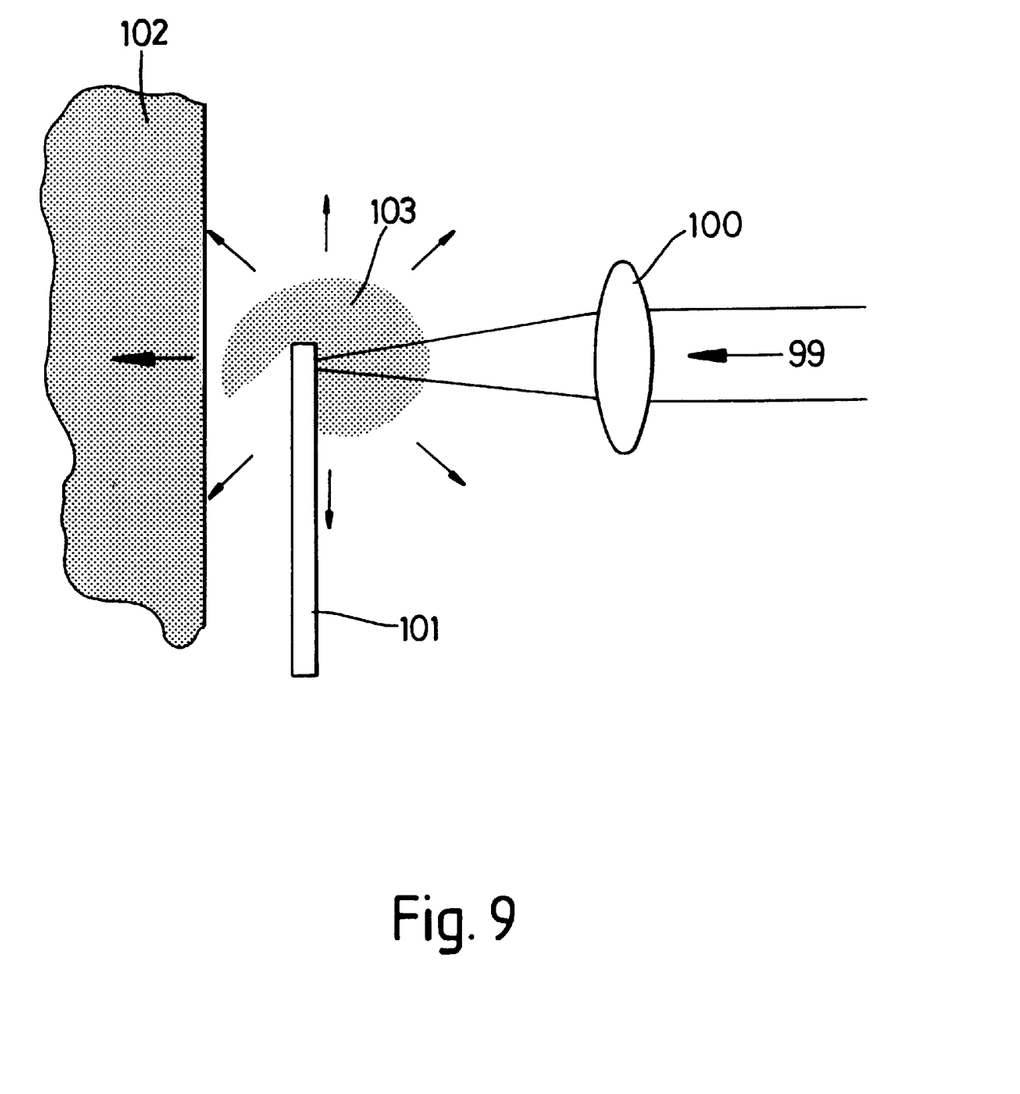
FIG. 9 shows schematically another way of generating ultrasound.

FIG. 9 shows a laser beam 99 focused by a lens 100 onto a target 101 in front of the sample 102 (or article) being tested. The laser beam 99 is thus totally blocked from the sample 102. The laser beam 99 generates a plasma 103 at the target 101. The plasma 103 is free to expand away from the point of impact on the target 101 and impacts on the sample 102. Thus only the plasma 103 is incident on the surface of the sample 102 where ultrasound is to be generated. This technique will predominantly generate longitudinal ultrasonic waves. A metal (e.g. stainless steel) target 5 mm thick, spaced a few mm from the sample is preferred.

We believe that satisfactory results can be achieved with a target—sample spacing in the range >0 mm to 10 mm, most preferably in the range 1 mm to 5 mm.

The thickness of the target is in part determined by the laser, but a thickness of about 0.1 to 5 mm is preferred.

The target may be damaged by the laser beam (or a hole made in it). This may mean that the target has to be moved between laser pulses to interpose a different part of the target, or different target. The target may be capable of obstructing direct impact from the laser beam for a large number of pulses, producing an acceptable plasma. If so it may not need moving between every pulse.

It will be appreciated that the transit time measurement that we perform does not measure the absolute height of liquid in a container, but rather the height of the surface above the ultrasound receiver. However, because we know the height of the receiver relative to the base of the container we can know the height of the surface of the liquid relative to the base of the container. It is necessary to have both the emitter and receiver of ultrasound below the level of the liquid in the container (because ultrasound of the required frequency content does not propagate well in air).

The ultrasound wave that is generated by the plasma has a spherical wavefront, and this is reflected by the gas-liquid interface as a reflection of the spherical wavefront.

We prefer to derive the first signal from the ultrasonic wave which has propagated from the generation location directly to the detection location in a known pathlength. We may in some circumstances prefer to use the signal derived from a reflected ultrasonic wave off the sides or bottom of the container which again has propagated via a known pathlength.

As the velocity of sound in a medium is dependent upon the temperature and composition of the medium a measurement of the actual transit time for a path of known length through the contents of the container will allow us to determine the height of the medium independent of the temperature and composition of the medium.

It will also be appreciated that if we use an EMAT as a receiver it cannot detect ultrasound unless the region of the container at which it detects is metallic, or has a metallic content. Foil-lined cardboard or plastic containers can be accommodated. Indeed, we may deliberately arrange for the containers to have a metal or metallic area or member at or in its wall at a region where, in use, the EMAT will be used as a detector. Because of the difficulty in orientating containers on a moving filling line we prefer to have the metal or metallic area or member extend completely around the periphery of the container.

The metal or metallic area or member may be provided on a label or sleeve of the container, possibly on the inner surface of the label or sleeve, possibly by having a metallic backing or band on the label or sleeve.

Other variations will now be described by way of further example.

Figure 10:
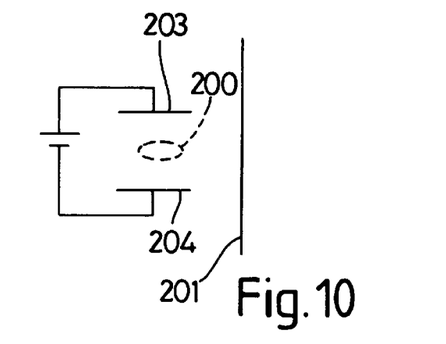
FIGS. 10 to 12 show schematically further ways of generating a plasma near the surface of a container.

FIG. 10 shows a pair of electrical discharge plates 203 and 204 adjacent a side wall of a can (again referenced 201). A discharge from one plate to the other creates a plasma, referenced 200, which generates ultrasound.

Figure 11:
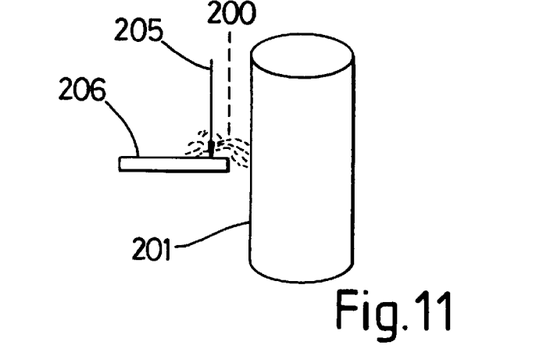

FIG. 11 shows a container 201 having ultrasound generated in it by momentum transfer from a plasma 200 generated by a laser beam 205 striking a plate-like target 206 extending radially to the container. The plasma 200 expands laterally off the target 206, in a direction generally parallel to the plane of the plate member 206 (of course without collimating means the plasma expands generally spherically, but is constrained by the plate 206). Collimating means, mechanical (e.g. plate(s) with holes in them) or magnetic guiding, or both may be provided.

Figure 12:
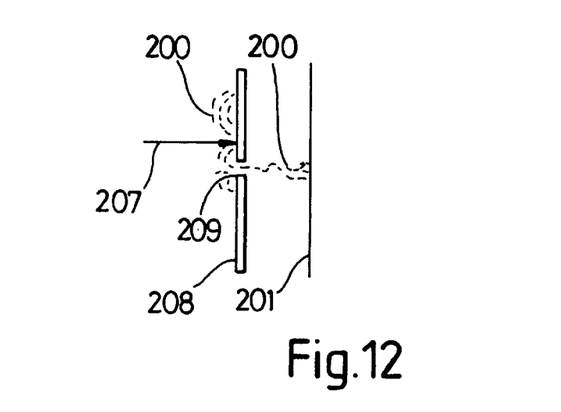

FIG. 12 shows a container surface 201 having ultrasound generated in it by plasma 200 generated by the impact of a laser beam 207 onto a plate 208. The plate 208 extends generally parallel to the central axis of the container and has a hole 209 in it. Plasma escapes through the hole 209 on to the container.

We may have a target-container separation of 30 mm or more. It is preferably less than 10 mm. However, it is desirable to have a minimum target-container separation in excess of 1 mm in order to ensure that the plasma has attained sufficient momentum normal to the surface of the container to generate ultrasound in the container contents with sufficient energy to perform the measurement.

We have appreciated that it is beneficial to generate plasma close to the edge of a target that also acts as a mask preventing the laser beam from directly striking the container. We prefer to confine the impact of the plasma to a localised region on the container; this produces the desired ultrasound source. In the arrangements of FIGS. 9 and 12 we prefer to have the laser beam strike the target as close to the edge of the target (or hole in the case of the arrangement of FIG. 12) as possible, consistent with ensuring that no portion of the laser beam directly impinges on the container. A distance of about 1 mm from the edge is referred.

The laser pulses used to generate ultrasound preferably have a rise time of about 100 ns or less, and have a pulse energy between 0.1 and 10 J.

The laser beam may be focused to a spot of about 5 mm diameter.

It should be made clear that although in many embodiments of the invention we have referred to "plasma" striking the container to generate ultrasound in the container (and hence in its contents) the plasma itself (as high energy ionised particles) need not reach the container still as a true plasma. The ions could reform as atoms—it is the momentum transfer that is important. Indeed after generating a plasma it may be that by the time the energy reaches the container there is only a supersonic (or possibly fast subsonic) shock wave in the air (or other gaseous medium surrounding the can) and little or no true plasma left. The invention does not therefore necessarily require ionised true plasma to strike the container. We may therefore wish "plasma generation means" to be read as "shock wave generation means" (non-mechanical contact, non-liquid contact).

It will be appreciated that we may choose to use the detection of the first "straight-through" wave to serve as an accurate reference point so that the transit time of the second "top-surface reflection" wave is accurately known (variation in delays in laser actuation, and ultrasound generation at the container are eliminated from the processing of the signals by using the time difference). We may then use that time difference to evaluate the height of the contents.

We may know the absolute transit time of the first wave through the contents of the container and the absolute transit time of the second wave through the contents of the container and subtract one from the other to determine the time difference between detection of the waves. Alternatively, we may use detection of the first wave as a reference point and measure the time between detection of the first wave and detection of the second wave.

The time difference between detection of the straight-through wave and detection of its reflection back from the opposite side of the container (two traverses of the diameter of the container) can be used, effectively, to determine the velocity of sound in the contents of the container (if the diameter of the container is known), thereby enabling the apparatus to work with containers with different contents, or with contents at different temperatures. We may use a knowledge of the time difference between detection of the straight-through wave and detection of the top surface reflection wave, and between the first detection of the straight-through wave and the detection of the reflection of that wave, in an appropriate algorithm.

What is claimed is:

1. A fill level monitoring apparatus adapted to monitor the height of contents in a container, comprising ultrasound generation means, an ultrasonic receiver and signal processing means adapted to receive signals from the receiver, the arrangement being such that the signal processing means identifies a first signal which is representative of a first ultrasonic wave which has travelled directly though the contents of the container to the receiver without reflection independently of the height of the contents in the container, and a second signal that is representative of a second ultrasonic wave that has been reflected from the interface between the upper surface of the contents in the container and the environment above the contents, and in which the signal processing means uses the difference in transit times for the two waves to provide an indication of the level of the contents in the container, and in which the first and second waves are part of the same ultrasonic wavefront in three dimensions.

2. A fill level monitoring apparatus according to claim 1, in which the ultrasound receiver is couplant free.

3. A fill level monitoring apparatus according to claim 1, in which the apparatus includes a broadband ultrasound receiver.

4. A fill level monitoring apparatus according to claim 3, in which the broadband ultrasound receiver can detect from low frequency to above 1 MHz.

5. A fill level monitoring apparatus according to claim 1, in which the receiver is an EMAT.

6. A fill level monitoring apparatus according to claim 5, in which the EMAT is polarised, to give maximum sensitivity to top surface reflections of ultrasound from the upper surface of the contents of the container.

7. A fill level monitoring apparatus according to claim 1, in which the receiver detects ultrasound from only a localised region in height of the container.

8. A fill monitoring apparatus according to claim 7 in which the container includes an exterior surface and the receiver detects ultrasound over a localised region of the container surface restricted to a vertical range of 4 mm or less.

9. A fill level monitoring apparatus according to claim 1, in which the apparatus is arranged such that the ultrasound receiver is disposed to a side of a container.

10. A fill level monitoring apparatus according to claim 1, in which the receiver is not more than 10 mm from the surface of the container when the ultrasound waves that generate the first and second signals are detected.

11. A fill level monitoring apparatus according to claim 1 in which the ultrasound generation means is adapted to generate simultaneously the ultrasound wave(s) which give rise to the first and second signals.

12. A fill level monitoring apparatus according to claim 1 in which the ultrasound generation means is adapted to generate at the same location on the container the ultrasound wave(s) which when detected generate the first and second signal.

13. A fill level monitoring apparatus according to claim 1 in which the ultrasound generation means is adapted to generate the ultrasound waves in a localised region in height of the container.

14. A fill level monitoring apparatus according to claim 1, in which the ultrasound generation means includes a laser.

15. A fill level monitoring apparatus according to claim 1 in which the ultrasound generation means is couplant free.

16. A fill level monitoring apparatus according to claim 1 in which the ultrasound generation means is capable of generating a broadband ultrasonic wave.

17. A fill level monitoring apparatus according to claim 1 in which the apparatus is arranged such that the ultrasound generation means is disposed to the side of the container.

18. A fill level monitoring apparatus according to claim 1 in which the receiver and generation means are on opposite sides of the container.

19. A fill level monitoring apparatus according to claim 1 in which when viewed from above the container the receiver and the generation means are at an angle away from the 180° straight-through configuration.

20. A fill level monitoring apparatus according to claim 1 in which the receiver and the generation means are at substantially the same height relative to the container.

21. A fill level monitoring apparatus according to claim 1 in which the receiver is at a different height to that of the generation means relative to the container.

22. A fill level monitoring apparatus according to claim 1 in which the container is moving during the transmission of the ultrasound waves that create the first signal, the second signal, or both signals.

23. A fill level monitoring apparatus according to claim 1 which is used with a container that is metallic or has a metal region.

24. A fill level monitoring apparatus according to claim 1, in which there is a feedback mechanism whereby the apparatus can feed back signals, derived from the first and second signals, to control apparatus for subsequent use in controlling the filling operation or filling apparatus.

25. A fill level monitoring apparatus according to claim 1 in which the apparatus has an electronic signal filter.

26. A fill level monitoring apparatus according to claim 1, in which the apparatus has a signal amplifier, which is tuned to the same band of frequencies as the receiver.

27. A container filling line comprising containing filling means adapted to deliver contents to a container, control means controlling the operation of the container filling means and fill-level monitoring apparatus adapted to monitor the height of content in a container, comprising an ultrasonic generation means, an ultrasound receiver and signal processing means adapted to receive signals from the receiver, the arrangement being such that the signal processing means identifies a first signal which is representative of a first ultrasonic wave which has been transmitted through the contents of the container independently of the height of the contents in the container directly from the ultrasonic generation means to the receiver, and a second signal that is representative of the second ultrasonic wave that has been reflected from the interface between the surface of the contents in the container and the environment above the contents, and in which the signal processing means uses the difference in transit times for the two waves to provide an indication of the level of the contents in the container.

28. A method of monitoring the fill level of contents in a container comprising generating ultrasound waves in the container, detecting a straight through ultrasound wave, detecting a top surface reflected wave from the top surface of the contents of the container, and measuring the time difference between the detection of the two waves in order to obtain an indication of the level of the contents in the container.

29. A method of monitoring the fill level of contents in a container according to claim 28 comprising using signal processing means to receive and identify a first signal which is representative of the straight through wave, and using the signal processing means to receive and identify a second signal which is representative of the top surface reflected wave, and wherein the signal processing means uses the arrival time of the first signal, and the pathlength of the straight through wave in the contents which is known from the dimensions of the container, in conjunction with the time difference between receipt of the first signal and receipt of the second signal to measure the height of the contents.

30. A method of monitoring the fill level of contents in a container comprising generating a first ultrasonic wave in the container and measuring its transit time to travel a first path directly through the contents of the container without reflection, from an ultrasonic generation means to an ultrasonic receiver that is independent of the level of contents in the container; generating a second ultrasonic wave in the container and measuring its transit time to travel a second path directly through the contents of the container that has a reflection from the surface of the contents of the container; and using the difference in transit time to evaluate the height to which the container is filled.

31. A fill level monitoring apparatus adapted to monitor the height of contents in a container, comprising an ultrasonic generator, an ultrasound receiver, and signal processing means adapted to receive signals from the receiver, the arrangement being such that the signal processing means identifies a first signal which is representative of a first ultrasonic wave which has been transmitted through the contents of the container independently of the height of the contents in the container, and a second signal that is representative of a second ultrasonic wave that has been reflected from the interface between the upper surface of the contents of the container and the environment above the contents, wherein the ultrasound generator is adapted to generate simultaneously the first and second ultrasonic waves and in which the signal processing means uses the difference in transit times for the two waves to provide an indication of the level of the contents in the container.

32. A fill level monitoring apparatus adapted to monitor the height of contents in a container, comprising an ultrasonic generator, an ultrasound receiver and signal processing means adapted to receive signals from the receiver, the arrangement being such that the signal processing means identifies a first signal which is representative of a first ultrasonic wave which has been transmitted through the contents of the container independently of the height of the contents in the container, and a second signal that is representative of a second ultrasonic wave that has been reflected from the interface between the upper surface of the contents of the container and the environment above the contents, in which the ultrasound generator is adapted to generate the ultrasound waves in a localized region in height of the container.

33. A fill line monitoring apparatus comprising container filling means adapted to deliver contents to a container, control means controlling the operation of the container filling means, an ultrasound generator, an ultrasound receiver and signal processing means adapted to receive signals from the receiver, the arrangement being such that the signal processing means identifies a first signal which is representative of a first ultrasonic wave which has been transmitted through the contents of the container independently of the height of the contents in the container, and a second signal that is representative of a second ultrasonic wave that has been reflected from the interface between the upper surface of the contents of the container, and in which the first and second waves are parts of the same ultrasonic wavefront in three dimensions.

34. A container filling line according according to claim 33 in which the first signal is representative of a wave that has travelled directly to the receiver without reflection.

35. A container filling line comprising containing filling means adapted to deliver contents to a container, control means controlling the operation of the container filling means and fill-level monitoring apparatus adapted to monitor the height of content in a container, comprising an ultrasonic generation means, an ultrasound receiver and signal processing means adapted to receive signals from the receiver, the arrangement being such that the signal processing means identifies a first signal which is representative of a first ultrasonic wave which has been transmitted through the contents of the container independently of the height of the contents in the container, and a second signal that is representative of the second ultrasonic wave that has been reflected from the interface between the surface of the contents in the container and the environment above the contents, and in which the signal processing means detects ultrasound from only a localized region in height of the container and uses the difference in transit times for the two waves to provide an indication of the level of the contents in the container.

* * * * *

UNITED STATES PATENT AND TRADEMARK OFFICE
CERTIFICATE OF CORRECTION

PATENT NO.   : 6,234,023 B1
DATED        : May 22, 2001
INVENTOR(S)  : Andrew P. Collins et al.

It is certified that error appears in the above-identified patent and that said Letters Patent is hereby corrected as shown below:

<u>Title page,</u>
Item [73], Assignee, please add -- The University of Warwick -- as the second Assignee.

Signed and Sealed this

Twentieth Day of May, 2003

JAMES E. ROGAN
*Director of the United States Patent and Trademark Office*